US00PP08679P

United States Patent [19]

Austin

[11] Patent Number: Plant 8,679

[45] Date of Patent: Apr. 12, 1994

[54] ROSE PLANT 'AUSWONDER'

[75] Inventor: David C. H. Austin, Wolverhampton, England

[73] Assignee: David Austin Roses Limited, Albrighton, England

[21] Appl. No.: 954,961

[22] Filed: Sep. 30, 1992

[51] Int. Cl.[5] ..... A01H 5/00

[52] U.S. Cl. ..... Plt./1

[58] Field of Search ..... Plt. 1, 25

*Primary Examiner*—Howard J. Locker
*Assistant Examiner*—E. F. McElwain
*Attorney, Agent, or Firm*—Klarquist, Sparkman, Campbell, Leigh & Whinston

[57] ABSTRACT

Shrub rose plant having a dwarf bushy growth and bearing lightly scented flowers of a distinctive apricot coloring.

1 Drawing Sheet

The present invention relates to a new and distinct variety of shrub rose plant of the Rosa hybrida class which was originated by me by crossing the variety Charles Austin, with the variety an unknown seedling.

The primary objective of this breeding was to produce a new rose variety having apricot, quartered, scented flowers on a bushy plant and which repeat flowers. The objective was substantially achieved along with other desirable improvements as evidenced by the following unique combination of characteristics which are outstanding in the new variety and which distinguish it from its parents, as well as from all other varieties of which I am aware:

1. Highly scented flowers;
2. Distinctive apricot coloring; and
3. Dwarf bushy plant.

Asexual reproduction of this new variety by budding, as performed in Albrighton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Charles Austin.

*Pollen parent.*—Seedling.

Classification:

*Botanical.*—Rosa hybrida.

*Commercial.*—Shrub.

FLOWER

Observations made from specimens grown in a garden environment at Albrighton, England in August 1991.

Blooming habit: Recurrent.

Bud:

*Size.*—0.75–1.25" long when the petals start to unfurl.

*Form.*—The bud form is globular, pointed ovoid.

*Color.*—When sepals first divide, the bud color is Brownish red 10D7. When half blown, the upper sides of the petals are pale orange 6A2-3, at the top, changing to pale orange 5A3; at the center; and the lower sides of the petals are the same as the upper side.

*Sepals.*—Color: Greyish green 29D7. Surface texture: Dull, leathery, tomentose. There are three normally appendaged sepals. There are two unappendaged sepals with hairy edges.

*Receptacle.*—Color: Deep green 29D8. Shape: Goblet shaped. Size: Small to medium, about $\frac{3}{8}$"×5/16". Surface: Smooth.

*Peduncle.*—Length 1–1$\frac{3}{4}$" (very variable). Surface: Glandular. Color: Deep green 29D8. Strength: Stiff, erect.

Bloom:

*Size.*—Medium. Average open size is 2$\frac{1}{2}$–3$\frac{1}{4}$" in diameter.

*Borne.*—Singly, several together in clusters of 2 to 20 flowers. If in clusters: Irregular shape.

*Stems.*—Medium. Average length is about 30 inches.

*Form.*—When first open: Bloom is cupped. Permanence: Flattens. Outer petal edges curl slightly.

*Petalage.*—Number of petals under normal conditions: Average 75.

*Color.*—The upper side of the petals is orange white 5A2 changing to pale orange/yellow 5A3 at the center. The reverse side of the petals is same as above. The color of the base is yellow 3A5. The major color on the upper side is pale orange/yellow 4A3–5A3.

*Variegations.*—None.

*Discoloration.*—The general tonality at the end of the first day: Slightly paler. At the end of the third day, the majority of petals are white 8A1, changing to yellowish white 3A2 at the center.

*Fragrance.*—Strong, citrus.

Petals:

*Texture.*—Thick, slightly fleshy.

*Shape.*—Deltoid, apex retuse.

*Form.*—Tips slightly recurved, edges slightly quilled.

*Arrangement.*—Imbricated, with few petaolids in the center.

*Persistence.*—Intermediate.

*Lastingness.*—On the plant: About 7 to 10 days. As a cut flower; Long, about 5 to 7 days.

Reproductive parts:

*Anthers.*—Size: Medium. Quantity: Many, average 105. Color: Yellow, 3A8–4A8 (vivid to deep yellow). Arrangement: Regular around styles, mixed with petaloids.

*Filaments.*—Color: Yellow, 12C8 cerise blush at base.

*Pollen.*—Color: Gold yellow.

*Styles.*—Color: Pale grey 30A3.

*Stigmas.*—Color: Yellow 3A5 and cerise 12C8 streaked at base.

Form: Shrub.

Growth: Medium, branching bushy.

Plant height: 30".

Stem length: 26".

Foliage: Number of leaflets on normal mid-stem leaves: 5.

*Size.*—Medium, about 1–2" long × ⅜–1¼" wide.

*Quantity.*—Normal.

*Color.*—New foliage: Deep-dark green 30E-F8. Old foliage: Dark green 29F8.

Leaflets:

*Shape.*—Oval, cuspidate apex.

*Texture.*—Upper side: Leathery.

*Edge.*—Serrated.

*Serration.*—Single or double.

*Petiole Rachis.*—Color: Brownish reddish 11D7 with parrot green 30E8 tinge.

*Petiole underside.*—1 to 3 per node and glandular hairs.

*Stipules.*—Serrated, about ¼–1" long (variable).

*Disease resistance.*—Resistant to mildew and blackspot under normal growing conditions at Albrighton, Wolverhampton, England.

Wood:

*New wood.*—Color: Light green. Grass green 30E7. Bark: Smooth.

*Old wood.*—Color: Deep-dark green 29E8 to 29E7 Bracken green. Bark: Smooth.

Prickles:

*Quantity.*—On main canes from base: Many. On laterals from main canes: Few.

*Form.*—Medium, hooked downward.

*Color when young.*—Green and red (9D5 rosewood).

*Position.*—Evenly spread.

Small Prickles:

*Quantity.*—On main stalks: None. On laterals: None.

I claim:

1. A new and distinct variety of shrub rose plant of the Rosa hybrida class, substantially as herein shown and described, characterized particularly as to novelty by the unique combination of its lightly scented flowers having a distinctive apricot coloring and dwarf bushy growth.

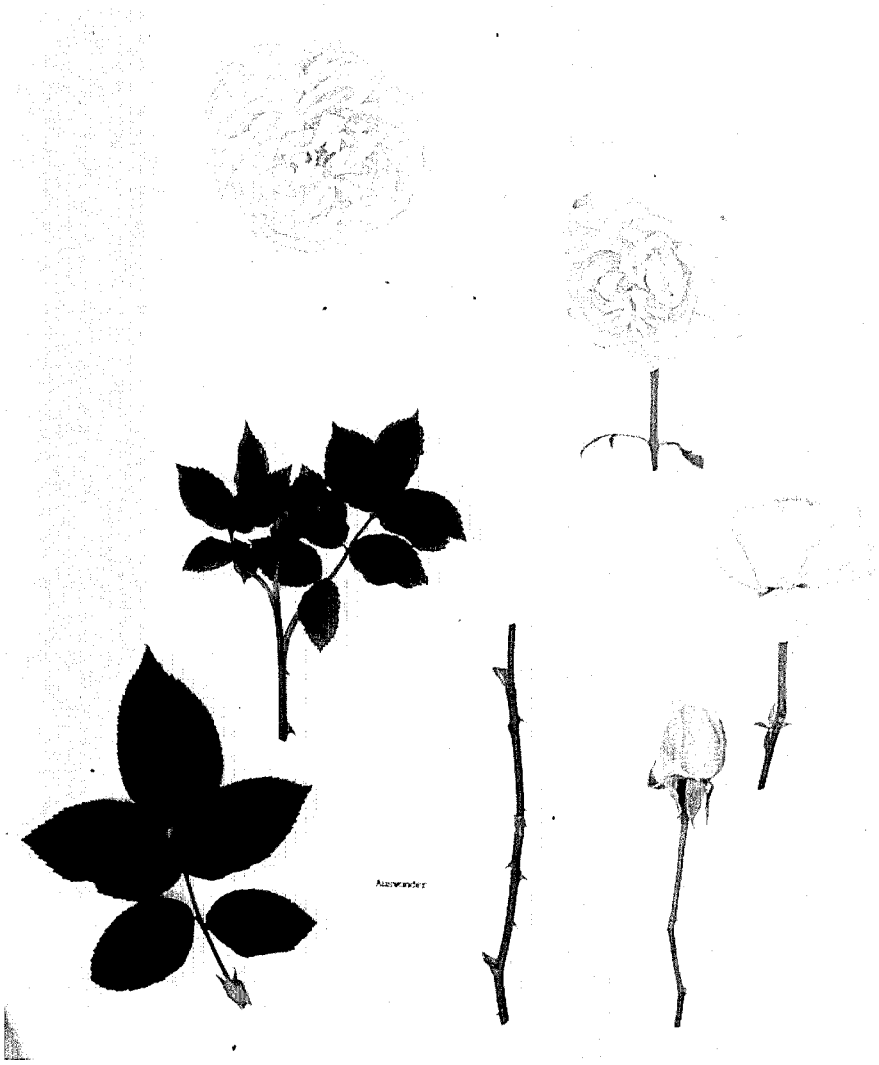

* * * * *